United States Patent
Ibert et al.

(10) Patent No.: US 11,208,221 B2
(45) Date of Patent: Dec. 28, 2021

(54) PROCESS FOR PACKAGING A DIANHYDROHEXITOL, AQUEOUS SOLUTION OF DIANHYDROHEXITOL PACKAGED AND USES THEREOF

(71) Applicant: Roquette Freres, Lestrem (FR)

(72) Inventors: Mathias Ibert, La Chapelle d'Armentieres (FR); Hervé Wyart, Cuinchy (FR); Emilie Josien, St. Venant (FR)

(73) Assignee: ROQUETTE FRERES, Lestrem (FR)

( * ) Notice: Subject to any disclaimer, the term of this patent is extended or adjusted under 35 U.S.C. 154(b) by 560 days.

(21) Appl. No.: 15/552,036

(22) PCT Filed: Feb. 18, 2016

(86) PCT No.: PCT/FR2016/050368
§ 371 (c)(1),
(2) Date: Aug. 18, 2017

(87) PCT Pub. No.: WO2016/132071
PCT Pub. Date: Aug. 25, 2016

(65) Prior Publication Data
US 2018/0037344 A1 Feb. 8, 2018

(30) Foreign Application Priority Data
Feb. 19, 2015 (FR) ....................... 1551411

(51) Int. Cl.
*B65B 3/04* (2006.01)
*B65D 65/42* (2006.01)
*B65B 7/00* (2006.01)
*A23L 3/00* (2006.01)
*A61K 31/34* (2006.01)
*C07D 493/04* (2006.01)

(52) U.S. Cl.
CPC ................ *B65B 3/04* (2013.01); *A23L 3/00* (2013.01); *A61K 31/34* (2013.01); *B65B 7/00* (2013.01); *B65D 65/42* (2013.01); *C07D 493/04* (2013.01); *A23V 2002/00* (2013.01)

(58) Field of Classification Search
CPC ...................................................... B65D 65/42
See application file for complete search history.

(56) References Cited

U.S. PATENT DOCUMENTS

| | | | |
|---|---|---|---|
| 5,750,223 A | 5/1998 | Tada et al. | |
| 2005/0014012 A1* | 1/2005 | Stapperfenne | C09D 175/06 428/480 |
| 2014/0158562 A1* | 6/2014 | Ibert | C07D 493/04 206/213.1 |
| 2015/0274745 A1* | 10/2015 | Hagberg | C07D 493/04 549/464 |

FOREIGN PATENT DOCUMENTS

| | | |
|---|---|---|
| CN | 101657533 A | 2/2010 |
| EP | 1 287 000 B1 | 10/2005 |
| EP | 2 354 175 A1 | 8/2011 |
| JP | S58-52032 A | 3/1983 |
| JP | H09-39975 A | 2/1997 |
| JP | 2003191935 A | 7/2003 |
| WO | WO 03/043959 A1 | 5/2003 |
| WO | WO 03/089445 A2 | 10/2003 |
| WO | 2008/116250 A1 | 10/2008 |
| WO | WO 2009/019371 A2 | 2/2009 |
| WO | WO 2012/042187 A1 | 4/2012 |
| WO | WO 2013/021126 A1 | 2/2013 |

* cited by examiner

Primary Examiner — Ian A Rummel
(74) Attorney, Agent, or Firm — Oliff PLC

(57) ABSTRACT

The present invention relates to a process for packaging a dianhydrohexitol, in the form of an aqueous solution in a container comprising a metal-based layer. It also relates to the container containing the aqueous solution of dianhydrohexitol.

13 Claims, No Drawings

PROCESS FOR PACKAGING A DIANHYDROHEXITOL, AQUEOUS SOLUTION OF DIANHYDROHEXITOL PACKAGED AND USES THEREOF

This application is a national stage of International Application No. PCT/FR2016/050368, filed on Feb. 18, 2016, which claims the benefit of French Patent Application 1551411, filed Feb. 19, 2015, the contents of each of which are incorporated herein by reference.

The present invention relates to a method for conditioning a dianhydrohexitol, in the form of an aqueous solution in a packaging material comprising at least one layer based on metal.

This is an extremely simple method in its implementation, and especially much less complex than the methods of the prior art which are essentially reserved for solid products, and which recommend using packaging materials which are impermeable to gases, and working under reduced oxygen and nitrogen pressure.

The method according to the present invention also proves to be inexpensive, which is another advantage. In addition, the applicant company has demonstrated that only a dianhydrohexitol in the form of an aqueous solution—and not a solid product—was able to be preserved in such a stable manner in this type of packaging comprising at least one layer based on metal.

The present invention also relates to the aqueous solution of dianhydrohexitol packaged in this way, and all the uses thereof, especially including those in the food and pharmaceutical fields.

Dianhydrohexitols, also referred to as isohexides, are products of the internal dehydration of hydrogenated C6 sugars (hexitols) such as sorbitol, mannitol and iditol. Among these doubly dehydrated hydrogenated sugars, isosorbide is currently the one for which most industrial applications are envisioned, especially in the sector of plastic materials, as intermediate in chemical synthesis, but also in the food and pharmaceutical fields.

For the majority of these applications, it is generally necessary to have compositions which are as pure as possible, having especially a content of dianhydrohexitols at least equal to 98.5% by weight, preferably at least equal to 99.5% by weight relative to the total dry matter thereof. Now, dianhydrohexitols and in particular isosorbide are extremely hygroscopic products which are chemically not very stable. The applicant company has in particular observed that the storage of isosorbide manufactured according to known methods, even sheltered from atmospheric moisture, could lead, under certain temperature conditions, to chemical degradation giving rise, inter alia, to the formation of formic acid, which is an acid which has a characteristic unpleasant odor, which is particularly bothersome in pharmaceutical or other applications.

The applicant company was thus motivated to develop methods for the purification and stabilization of dianhydrohexitols, described especially in the patent applications EP 1 287 000 and WO 03/043959. The inventions relating to these applications cover both solid dianhydrohexitols and dianhydrohexitols in liquid form. A stable liquid composition of isosorbide with a dry matter content of between 50% and 90% is disclosed in the document WO 03/043959. As such, only the stability of solid products was evaluated in these two applications, by storage of test specimens in a container respectively made of plastic in polyethylene bags (EP 1 287 000) and made of glass (WO 03/043959) at a temperature equal to 60° C. and 40° C., respectively.

Subsequently, the applicant company noticed that the durations for preserving the solid dianhydrohexitols, determined under the conditions of the tests described in patent applications EP 1 287 000 and WO 03/043959, gave only a poor reflection of the stability of these same products under real conditions of transport and storage. The applicant company noted in particular relatively large concentrations of formic acid close to the polyethylene film conventionally serving to package dianhydrohexitols in solid form, and especially isosorbide in the powder state.

The applicant company then observed that by substantially increasing the concentration of antioxidants in the layer of plastic material in contact with the dianhydrohexitol, the stability thereof was substantially improved, especially when the dianhydrohexitol in question was isosorbide. This invention was protected in patent application WO 2009/019371, the plastic packaging material being selected from polyethylene, polypropylene and copolymers of ethylene and of propylene. Here, the term "antioxidant" covers the same meaning as in the document WO 2009/019371, namely it encompasses all the compounds capable of limiting or of suppressing thermooxidative degradation, also known by the term autoxidation, of organic compounds, in particular of organic polymers.

It should be noted that the method for packaging which is the subject of said application applies to liquid or solid dianhydrohexitols, even if the solid form is favored, and that a most preferred variant consists in packaging the dianhydrohexitol under an anhydrous and/or inert atmosphere, for example under a nitrogen atmosphere. This document stipulates that, in order to guarantee optimum stability of the dianhydrohexitol during transport and storage, it is necessary to provide an additional layer of protection against oxygen in the air, steam and/or light.

In addition, it is worth noting that this type of solution does not make it possible to condition dianhydrohexitols for food or pharmaceutical applications, which both require heavily reduced amounts of antioxidants. By way of example, the FDA (Food and Drug Agency) produces an official list of the only antioxidants and stabilizers authorized for these two applications, with all the corresponding restrictions in terms of amounts, as a function of the polymer material in which they are incorporated.

Independently of this food or pharmaceutical context, the technical solutions developed in the preceding invention proved to require the development of complex conditioning materials and only applied to small amounts (approximately ten grams) of dianhydrohexitols, the problem of compacting of the dianhydrohexitols during their storage in bags of several kilograms or even several tens of kilograms remaining unsolved.

The latter problem was solved in the patent application WO 2013/021126 through the development of a method for packaging dianhydrohexitol in a conditioning material impermeable to gases, characterized in that the oxygen partial pressure within the conditioning is between 0.1 mbar and 10 mbar. A preferred variant consists in also limiting the nitrogen partial pressure within the conditioning to between 240 and 1012.9 mbar. It is indeed mentioned that these types of conditioning are suitable both for dianhydrohexitols in liquid form and solid form.

That being said, the document WO 2012/042187 indicates that for dianhydrohexitols in solid form, even if the latter are purified, stabilized and conditioned according to the techniques described above, it is still necessary to shape them into pellets to be entirely certain that the phenomenon of caking will be avoided, which phenomenon is particularly bothersome in operations of transport, handling and especially transferring of the products.

If the path of studies by the applicant company, as laid out above, is followed, the current prevailing solution for stable conditioning over time of the dianhydrohexitols therefore consists in using materials impermeable to gases, under reduced oxygen pressure, or even also under limited nitrogen pressure. It is readily appreciated that such an approach is both long and costly. Moreover, for dianhydrohexitols in powder form, it is suitable to provide, in addition to the abovementioned operations, a step of pelletizing with a view to avoiding problems of caking.

Now, and against all expectations, the applicant company has been able to observe, following numerous studies, that there is a very simple way to condition dianhydrohexitols in an extremely stable manner over time. This method relies on the conditioning of said dianhydrohexitol in the form of an aqueous solution in a packaging material comprising at least one layer based on metal. Surprisingly, the applicant has observed that the stability of a dianhydrohexitol conditioned in liquid form in this way is much better than that of a solid dianhydrohexitol packaged according to the prior art cited above.

This is all the more surprising since it goes against the teaching according to which it is necessary to rely on conditioning materials impermeable to gases, under reduced oxygen pressure, or even also under limited nitrogen pressure.

Moreover and entirely advantageously, by removing the antioxidants in the packaging material, food and pharmaceutical applications become feasible, which was not certain in the case of the document WO 2009/019371 which recommends working with at least 0.1% by weight of these additives in the packaging barrier layer.

This is therefore a conditioning method which is particularly simple to implement, very inexpensive and perfectly suited to aqueous solutions of dianhydrohexitol. This method makes it possible especially to package and condition aqueous solutions of dianhydrohexitol in an extremely stable manner over time. In the present application, this stability is understood very simply through monitoring the change in the pH of said composition over time. A significant change or shift in this pH is proof of the phenomenon of oxidation of the dianhydrohexitol, which will lead to the formation of formic acid. Finally, dianhydrohexitols are advantageously made available, which may be packaged, handled and transported within the context of final applications in the food and pharmaceutical sectors.

The method which is the subject of said application therefore relates to a method for conditioning a dianhydrohexitol, comprising:
providing an aqueous solution of dianhydrohexitol,
introducing said aqueous solution of dianhydrohexitol into a container,
then closing said container,
in which the surface of the container in contact with the aqueous solution of dianhydrohexitol consists of a layer based on metal, optionally covered by a layer of varnish based on polyester resin or epoxy resin.

The expression "aqueous solution of dianhydrohexitol" denotes a composition containing essentially water and at least one dianhydrohexitol. It is especially characterized by the dry matter content thereof, expressed as % dry weight relative to the total weight thereof. The latter is especially between 40% and 95%, preferentially between 50% and 90%, very preferentially between 60% and 85%. It is moreover suitable not to associate said aqueous solution of dianhydrohexitol with another liquid form of dianhydrohexitol: namely a melt of dianhydrohexitol, that is to say a dianhydrohexitol in a molten state at a temperature of greater than or equal to 63+−2° C. (at atmospheric pressure).

Generally, dianhydrohexitols are synthesized in the presence of water (or water is generated during their synthesis): by recovering said dianhydrohexitol in this reaction medium, this immediately gives an aqueous solution of dianhydrohexitol which can be used according to the invention. The solutions of dianhydrohexitols may especially be obtained according to the methods described in the abovementioned patent applications EP 1 287 000 and WO 03/043959. It is possible to choose to retain all or some of the water used during the preparation of the dianhydrohexitol or to eliminate all the water to obtain a product in solid form which will be returned to aqueous solution by simply adding water, which constitutes another possibility for preparing an aqueous solution of dianhydrohexitol which can be used according to the invention.

The aqueous solution in question may contain a single dianhydrohexitol, just as it may contain several thereof. These dianhydrohexitols (1,4:3,6-dianhydrohexitols) encompass isosorbide (1,4:3,6-dianhydrosorbitol), isomannide (1,4:3,6 dianhydromannitol), isoidide (1,4:3,6-dianhydroiditol) and mixtures of at least two of these products. The aqueous solution preferably only contains a single dianhydrohexitol, which is isosorbide.

"Method for conditioning" is intended to mean an operation which consists in placing a product in a container, with which it is in direct contact, in order to facilitate the protection and preservation thereof.

The term "layer" denotes, in the present application, a uniform casing; the term "layer based on metal" means that it consists predominantly of said metal (said metal then representing at least 90% by weight, preferentially 99%, very preferentially 100% by weight of the total weight of said "layer").

The term "metal" denotes a material, the cohesion of the atoms of which is ensured by metallic bonding: all the atoms of the object share one or more electrons with one another. More specifically, and with reference to the periodic table of the elements, the diagonal line going from boron (B) down to polonium (Po) separates the metallic elements (downwards and to the left) from the non-metallic elements (upwards and to the right).

The layer based on metal may also is composed of an alloy, that is to say a combination of a metallic element with one or more other chemical elements making it possible to increase the mechanical or chemical strength. Mention may be made, for example, of steel (mainly composed of iron and carbon) or stainless steel, for which chromium, and optionally other metals such as nickel, molybdenum, silicon, manganese, titanium, vanadium or tungsten are added.

According to a first variant of the method forming the subject of the present application, the surface of the container in contact with the aqueous solution of dianhydrohexitols consists of a layer based on metal. This layer is preferably made of metal (consisting to 100% of said metal).

According to a second, preferred, variant, the surface of the container in contact with the aqueous solution of dianhydrohexitols consists of a layer based on metal covered by a layer of varnish.

According to this variant, the layer of varnish is in contact with the aqueous solution of dianhydrohexitol.

The varnish is based on polyester resin or epoxy resin, for example of epoxy-phenol type. The varnish is applied in liquid form and cured by heating over the metal layer of the container in order to form a dry film.

The thickness of the layer of the container in contact with the aqueous solution of dianhydrohexitol does not play a decisive role in the present invention. It may especially be between 50 μm and 1 cm. The container is preferably a rigid material so as to be able to withstand the stresses linked to the packaging of a product in liquid form such as the aqueous solution according to the present invention. It may be a barrel, a container, a tank, but more generally it is thus a rigid container of any shape and size whatsoever.

The wall of the container may consist of one or more layers. For example, the wall of the container may be a single layer based on metal, especially on aluminum or on stainless steel, or multiple layers comprising at least two layers, especially a layer of metal and a layer of resin-based varnish.

The method according to the present invention thus comprises introducing, into the container described above, the aqueous solution of dianhydrohexitol described above. This introduction is carried out by any means well known to those skilled in the art, especially means suited to the handling and transfer of products in liquid form, especially of compositions of dianhydrohexitol in liquid form. These means are, for example, gravity filling from a storage tank located above the packaging material by means of a filling orifice, or by means of pumping equipment to transfer the aqueous solution of dianhydrohexitol from the tank to the packaging material.

The container is then closed. This closure takes place by virtue of devices known to those skilled in the art and adapted to the shape of the material in question. These devices are for example the closure of the filling orifice by means of a screw cap or crimping by means of a crimper.

A second subject of the present invention relates to an aqueous solution of dianhydrohexitol conditioned in a container, the surface of the container in contact with the aqueous solution of dianhydrohexitols consisting of a layer based on metal, optionally coated with a varnish based on polyester resin or epoxy resin.

In other words, the invention relates to a container containing an aqueous solution of dianhydrohexitol, the surface of the container in contact with the aqueous solution of dianhydrohexitol consisting of a layer based on metal, optionally coated with a varnish based on polyester resin or epoxy resin. More particularly, the surface of the container in contact with the aqueous solution of dianhydrohexitols consists of a layer based on metal covered with a layer of varnish based on polyester resin or epoxy resin, said epoxy varnish preferably being of epoxy-phenol type.

In this context, the aqueous solution of dianhydrohexitol, on the one hand, and the layer based on metal, on the other, assume all the features listed above relating to the method which constitutes the first subject of the present application.

The present invention makes it possible to improve the storage stability of aqueous solutions of dianhydrohexitol, especially a pH variation of less than 10% after two months, preferably after three months, at 50° C. Consequently, the amount of antioxidants and stabilizers can be reduced.

Thus, this second subject according to the invention may also be characterized in that the dianhydrohexitol is chosen from isosorbide, isomannide, isoidide, or mixtures of at least two of these products, and is preferentially isosorbide.

According to this same subject, the aqueous solution of dianhydrohexitol is also characterized in that it has a dry matter content of between 40% and 95%, preferentially between 50% and 90%, very preferentially between 60% and 85% relative to the total weight thereof.

The container containing the aqueous solution of dianhydrohexitol may then be used in plastics applications, as a synthesis intermediate, or in the food and pharmaceuticals sectors. This means that said container containing said aqueous solution is able to be entirely or partially emptied in order to recover all or some of the aqueous solution of dianhydrohexitol which it contains. Said solution then serves for the preparation of materials, especially in the plastics sector, or for the manufacture of intermediates for chemical synthesis, but also in the food and pharmaceuticals fields.

The invention will be better understood in the light of the following examples which are in no way limiting.

EXAMPLES

The following examples illustrate the benefit of the packaging method according to the invention, by demonstrating that it enables packaging of a composition of dianhydrohexitol (isosorbide in the case in point) which remains very stable over time, as evidenced by the change in pH thereof.

Not only does the pH of the liquid composition of isosorbide remain stable over several months, regardless of the storage conditions, but it is even more stable than the pH of the same composition of isosorbide in solid form.

Example 1

This example relates to the packaging and storage of isosorbide, in solid or liquid form, said isosorbide having been stabilized beforehand with disodium phosphate.

The procedure begins first of all by manufacturing a solid isosorbide composition and a liquid isosorbide composition, in the following way:

1 kg of a solution of sorbitol at 70% of dry matter sold by the applicant company under the name Neosorb 70/02 and 7 g of concentrated sulfuric acid are introduced into a jacketed stirred reactor. The mixture obtained is heated under vacuum (pressure of approximately 100 mbar) for 5 hours so as to eliminate the water contained in the initial reaction medium and that originating from the sorbitol dehydration reaction.

The reaction crude is then cooled to 100° C. and then neutralized with 11.4 g of a 50% (by weight) sodium hydroxide solution. The isosorbide composition neutralized in this way is then distilled under vacuum (pressure lower than 50 mbar).

The slightly colored (light yellow color) crude isosorbide distillate is then dissolved in 2-propanol, at a temperature of 60° C., so as to obtain a solution with 75% DM. This solution is then cooled slowly, over the course of 5 hours, down to a temperature of 10° C. A recrystallized isosorbide seed is added at 40° C.

The crystals are then drained in a centrifuge and washed with 2-propanol. After drying under vacuum, the crystals are redissolved in water so as to obtain a DM of 40%.

This solution is then percolated on a column of granular active carbon CPG 12-40 at a rate of 0.5 BV/h (Bed Volume/hour). The decolored isosorbide composition thus obtained is then passed, at a rate of 2 BV/h, successively over a column of Purolite C 150 S strong cationic resin and then a column of Amberlite IRA 910 strong anionic resin. This solution is then treated with powdered active carbon of Norit SX+ type at 20° C. for 1 hour. The active carbon is used in a proportion of 0.5% expressed by dry weight/dry weight of solution.

0.005% of disodium phosphate (stabilizer) (dry weight/dry weight of isosorbide contained in the composition) is then introduced into said composition.

After filtration, the isosorbide solution is concentrated under vacuum. The solution is concentrated until a solution with 80% dry matter is obtained. A portion of the solution is recovered in order to carry out tests 4, 5 and 6. The concentration under vacuum of the remainder of the solution is then carried out, in order to eliminate the residual water. The molten mass obtained crystallizes on cooling in the form of a massed product of large crystals which is subsequently ground to obtain a white-colored powder having a moisture content of 0.2%. This powder is recovered for tests 1, 2 and 3.

These different compositions then serve to illustrate the packaging method according to the invention or according to the prior art.

Test No. 1

This test relates to the prior art and illustrates the packaging of the solid isosorbide composition in a "PE+Alu" conditioning. More specifically, this conditioning consists of a first inner bag (20 cm×20 cm) made of polyethylene (PE) with a thickness of 100 µm, combined with a second outer bag (25 cm×25 cm) consisting of an aluminum complex (Alu) containing 80 µm thick polyethylene covered with 8.5 µm thick aluminum.

The isosorbide composition is packaged in the following manner: 100 g of the solid isosorbide composition as obtained above are introduced into the inner PE bag which is closed by sealing using an impulse heat sealer (SZ 380 model sold by Joisten & Kettenbaum GmbH & Co, Bergisch Gladbach, Germany). This bag is itself placed inside the outer bag Alu, which is then closed by sealing with the same heat sealer in order to ensure leaktightness with regard to the outer atmosphere.

Test No. 2

This test relates to the prior art and illustrates the packaging of the solid isosorbide composition in a conditioning consisting of "white PE BigBag Liner/alu/PET". More specifically, this conditioning consists of a bag (25 cm×25 cm) consisting of a complex of total thickness of approximately 100 µm consisting of an inner layer made of polyethylene (PE) with a thickness of 80 µm, an intermediate layer made of aluminum with a thickness of 9 µm and an outer layer made of polyethylene terephthalate (PET) with a thickness of 12 µm.

The isosorbide composition is packaged in the following manner: 100 g of the solid isosorbide composition as obtained above are introduced into the "white PE BigBag Liner/alu/PET" bag which is closed by sealing using an impulse heat sealer (SZ 380 model sold by Joisten & Kettenbaum GmbH & Co, Bergisch Gladbach, Germany) in order to ensure leaktightness with regard to the outer atmosphere.

Test No. 3

This test relates to the prior art and illustrates the packaging of the solid isosorbide composition in a conditioning consisting of "carbon PE+Alu". More specifically, this conditioning consists of a first inner bag (20 cm×20 cm) made of carbon-additivated polyethylene (carbon PE) with a thickness of 150 µm, and a second, outer, bag (25 cm×25 cm) consisting of an aluminum complex (Alu) containing 80 µm thick polyethylene covered with 8.5 µm thick aluminum.

The isosorbide composition is packaged in the following manner: 100 g of the solid isosorbide composition as obtained above are introduced into the inner carbon PE bag which is closed by sealing using an impulse heat sealer (SZ 380 model sold by Joisten & Kettenbaum GmbH & Co, Bergisch Gladbach, Germany). This bag is itself placed inside the outer bag Alu, which is then closed by sealing with the same heat sealer in order to ensure leaktightness with regard to the outer atmosphere.

Test No. 4

This test relates to the invention and illustrates the packaging of the liquid isosorbide composition in aluminum conditioning, referred to as "Alu". More specifically, this conditioning is a 300 ml pure aluminum flask (>99.5% of aluminum). A flask of this type is sold especially by VWR under the reference 215-0261 or by Burkle under the reference 0327-0300.

The isosorbide composition is packaged in the following manner: 100 g of the liquid isosorbide composition as obtained above are poured into the aluminum flask which is closed by screwing on a plastic cap equipped with an internal seal, also made of aluminum, in order to ensure leaktightness with regard to the outer atmosphere.

Test No. 5

This test relates to the invention and illustrates the packaging of the liquid isosorbide composition in a stainless steel conditioning, referred to as "Inox".

More specifically, this conditioning is a 355 ml 18/8 (18% chromium 8% nickel) stainless steel flask. Such a flask is sold especially by sans-BPA.com under the reference 09.01.10.01, with a Loop Inox PP5 cap.

The isosorbide composition is packaged in the following manner: 100 g of the liquid isosorbide composition as obtained above are poured into the stainless steel flask which is closed by screwing on a cap, also made of stainless steel, in order to ensure leaktightness with regard to the outer atmosphere.

Test No. 6

This test relates to the invention and illustrates the packaging of the liquid isosorbide composition in a metal conditioning coated with an epoxy layer, referred to as "Metal Epoxy". More specifically, this conditioning consists of a 150 ml steel flask coated with an epoxy-phenol resin.

The isosorbide composition is packaged in the following manner: 100 g of the liquid isosorbide composition as obtained above are poured into the epoxy metal flask which is closed by crimping on a cover also made of steel coated with an epoxy-phenol resin using a crimper (Sertibasic 132 model, sold by SCIM, Casteljaloux, France). Such a flask is especially sold by Temaco under the reference 120619.

The solid and liquid isosorbide compositions packaged according to tests 1 to 6 are placed in a ventilated oven, thermostated at the temperature of 50° C. Several conditionings per test are placed in the oven in order to monitor the change in pH of each composition over time.

The change in pH of each composition over time is monitored in the following way: firstly, for each solid or liquid isosorbide composition, all the sample is extracted from the conditioning materials and is added to osmosed water in order to obtain a solution of isosorbide with 40% dry matter in osmosed water, then the initial pH of this solution is measured. The pH measurement is carried out on a pH meter of Radiometer Analytical PHM 220 brand equipped with a combined Ag/AgCl wire electrode of Mettler Toledo brand, calibrated beforehand using pH 7 and 4 buffer solutions. After a determined period of storage at 50° C., a solution of isosorbide with 40% dry matter is prepared in the same way in osmosed water for each solid or liquid isosorbide composition, then the pH is measured using the same pH meter. The results are given in table 1.

TABLE 1

| Test No. | 1 | 2 | 3 | 4 | 5 | 6 |
|---|---|---|---|---|---|---|
| Packaging | White PE + Alu | White PE BigBag Liner/alu/PET | Carbon PE + Alu | Alu | Inox | Epoxy Metal |
| Physical form | Solid | Solid | Solid | Liquid | Liquid | Liquid |
| pH 0 day | 7.2 | 7.6 | 7.2 | 7.4 | 7.4 | 7.4 |
| pH 1 month | 3.1 | 3.9 | 3.2 | 7.8 | 7.3 | 7.5 |
| pH 2 months | | | | 7.0 | 4.9 | 7.5 |

These results demonstrate clearly that the aqueous solution of isosorbide conditioned according to the invention in an "Inox", "Alu" and "Epoxy Metal" packaging is much more stable than the solid isosorbide conditioned in the "PE+Alu", "white PE BigBag Liner/alu/PET" and "carbon PE+Alu" packaging.

Example 2

This example relates to the packaging and storage of isosorbide, in solid or liquid form, said isosorbide having been stabilized beforehand with diethanolamine.

The procedure begins first of all by manufacturing a liquid isosorbide composition and a solid isosorbide composition in the same way as for example 1, except for the fact that the disodium phosphate is replaced by 0.0025% of diethanolamine by dry weight relative to the dry weight of isosorbide.

The liquid and solid compositions obtained as above then serve to illustrate the packaging method according to the invention or according to the prior art.

In this example, the flasks according to the invention are the same as those described in the preceding example.

Test No. 7

This test relates to the prior art and illustrates the packaging of the solid isosorbide composition in a "PE+Alu" conditioning. More specifically, this conditioning consists of a first inner bag (20 cm×20 cm) made of polyethylene (PE) with a thickness of 100 µm, combined with a second outer bag (25 cm×25 cm) consisting of an aluminum complex (Alu) containing 80 µm thick polyethylene covered with 8.5 µm thick aluminum.

The isosorbide composition is packaged in the following manner: 100 g of the solid isosorbide composition as obtained above are introduced into the inner PE bag which is closed by sealing using an impulse heat sealer (SZ 380 model sold by Joisten & Kettenbaum GmbH & Co, Bergisch Gladbach, Germany). This bag is itself placed inside the outer bag Alu, which is then closed by sealing with the same heat sealer in order to ensure leaktightness with regard to the outer atmosphere.

Test No. 8

This test relates to the prior art and illustrates the packaging of the solid isosorbide composition in a conditioning consisting of "white PE BigBag Liner/alu/PET". More specifically, this conditioning consists of a bag (25 cm×25 cm) consisting of a complex of total thickness of approximately 100 µm consisting of an inner layer made of polyethylene (PE) with a thickness of 80 µm, an intermediate layer made of aluminum with a thickness of 9 µm and an outer layer made of polyethylene terephthalate (PET) with a thickness of 12 µm.

The isosorbide composition is packaged in the following manner: 100 g of the solid isosorbide composition as obtained above are introduced into the "white PE BigBag Liner/alu/PET" bag which is closed by sealing using an impulse heat sealer (SZ 380 model sold by Joisten & Kettenbaum GmbH & Co, Bergisch Gladbach, Germany) in order to ensure leaktightness with regard to the outer atmosphere.

Test No. 9

This test relates to the invention and illustrates the packaging of the liquid isosorbide composition in aluminum conditioning, referred to as "Alu". More specifically, this conditioning is a 300 ml pure aluminum flask (>99.5% of aluminum).

The isosorbide composition is packaged in the following manner: 100 g of the liquid isosorbide composition as obtained above are poured into the aluminum flask which is closed by screwing on a plastic cap equipped with an internal seal, also made of aluminum in order to ensure leaktightness with regard to the outer atmosphere.

Test No. 10

This test relates to the invention and illustrates the packaging of the liquid isosorbide composition in a stainless steel conditioning, referred to as "Inox".

More specifically, this conditioning is a 355 ml 18/8 (18% chromium-8% nickel) stainless steel flask.

The isosorbide composition is packaged in the following manner: 100 g of the liquid isosorbide composition as obtained above are poured into the stainless steel flask which is closed by screwing on a cap, also made of stainless steel, in order to ensure leaktightness with regard to the outer atmosphere.

Test No. 11

This test relates to the invention and illustrates the packaging of the liquid isosorbide composition in a metal conditioning coated with an epoxy layer, referred to as "Metal Epoxy". More specifically, this conditioning consists of a 150 ml steel flask coated with an epoxy-phenol resin.

The isosorbide composition is packaged in the following manner: 100 g of the liquid isosorbide composition as obtained above are poured into the epoxy metal flask which is closed by crimping on a cover also made of steel coated with an epoxy-phenol resin using a crimper (Sertibasic 132 model, sold by SCIM, Casteljaloux, France).

The solid and liquid isosorbide compositions packaged according to tests 7 to 11 are placed in a ventilated oven, thermostated at the temperature of 50° C. Several conditionings per test are placed in the oven in order to monitor the change in pH of each composition over time.

The change in pH of each composition over time is monitored according to the same protocol as for example 1.

The results are given in table 2. As for example 1, it is observed that the aqueous solutions of isosorbide packaged according to the invention are much more stable than the solid compositions of isosorbide packaged according to the prior art.

TABLE 2

| | Test No. | | | | |
|---|---|---|---|---|---|
| | 7 | 8 | 9 | 10 | 11 |
| Packaging | White PE + Alu | White PE Big Bag Liner/alu/PET | Alu | Inox | Epoxy metal |
| Physical form | Solid | Solid | Liquid | Liquid | Liquid |
| pH 0 day | 8.1 | 8.4 | 8.5 | 8.5 | 8.5 |
| pH 1 month | 6.5 | 7.5 | 8.3 | 8.3 | 8.2 |
| pH 2 months | 3.2 | 7.5 | 8.3 | 8.2 | 8.2 |
| pH 3 months | | 3.2 | 7.1 | 6.9 | 7.0 |

The invention claimed is:

1. A method for conditioning a dianhydrohexitol, comprising:
providing an aqueous solution of dianhydrohexitol,
introducing said aqueous solution of dianhydrohexitol into a container having an interior surface, and
then closing said container with the aqueous solution of dianhydrohexitol in direct contact with the interior surface, said interior surface consisting of a layer based on metal, optionally covered by one of a polyester resin and epoxy resin based varnish,
wherein an oxygen pressure inside the closed container is not a reduced oxygen pressure.

2. The method as claimed in claim 1, wherein the dianhydrohexitol is selected from the group consisting of isosorbide, isomannide, isoidide, and mixtures of at least two of these products.

3. The method as claimed in claim 1, wherein the aqueous solution of dianhydrohexitol has a content of dry matter of between 40% and 95%, relative to a total weight thereof.

4. The method according to claim 3, wherein the aqueous solution of dianhydrohexitol has a content of dry matter of between 50% and 90% relative to the total weight thereof.

5. The method as claimed in claim 1, wherein the layer based on metal is covered by one of a polyester resin and epoxy resin based varnish.

6. The method according to claim 1, wherein said metal comprises one of aluminum and steel.

7. A closed container containing an aqueous solution of dianhydrohexitol, said container having an interior surface in direct contact with the aqueous solution of dianhydrohexitol, said interior surface consisting of a layer based on metal, optionally coated with a varnish based on one of a polyester resin and an epoxy resin, wherein an oxygen pressure inside the closed container is not a reduced oxygen pressure.

8. The closed container containing an aqueous solution of according to claim 7, wherein said metal based layer is covered by an epoxy-phenol based varnish.

9. A packaged article, said article including a closed container with an aqueous solution of dianhydrohexitol in direct contact with an interior surface of said container, said interior surface is formed from a metal layer, and an optional varnish layer covering said metal, wherein said dianhydrohexitol directly contacts one of said layers, and wherein an oxygen pressure inside the closed container is not a reduced oxygen pressure.

10. The article of claim 9, wherein said metal comprises one of aluminum and steel.

11. A method of producing a product from a dianhydrohexitol precursor, comprising:
providing a closed container of the precursor, said precursor comprising an aqueous solution of dianhydrohexitol which is in direct contact with an interior surface of the container, wherein the interior surface is formed from at least one of a metal layer and a varnish layer and wherein an oxygen pressure inside the closed container is not a reduced oxygen pressure; and
recovering said stored dianhydrohexitol for producing said product.

12. The method according to claim 11, wherein said dianhydrohexitol precursor is selected from the group consisting of isosorbide, isomannide, isoidide, and mixtures of at least two of said dianhydrohexitol precursors.

13. The method according to claim 6, wherein the wall of the container is a single layer based on aluminum.

* * * * *